(12) United States Patent
Mosca

(10) Patent No.: US 7,662,608 B2
(45) Date of Patent: *Feb. 16, 2010

(54) CHRONIC PATHOGEN-EXPRESSING CELL LINES

(75) Inventor: Joseph D. Mosca, Ellicott City, MD (US)

(73) Assignee: JDM Technologies, Inc., Ellicott City, MD (US)

( * ) Notice: Subject to any disclaimer, the term of this patent is extended or adjusted under 35 U.S.C. 154(b) by 215 days.

This patent is subject to a terminal disclaimer.

(21) Appl. No.: 10/486,415

(22) PCT Filed: Sep. 24, 2002

(86) PCT No.: PCT/US02/30197

§ 371 (c)(1),
(2), (4) Date: Feb. 6, 2004

(87) PCT Pub. No.: WO03/027269

PCT Pub. Date: Apr. 3, 2003

(65) Prior Publication Data

US 2005/0074881 A1      Apr. 7, 2005

Related U.S. Application Data

(60) Provisional application No. 60/324,835, filed on Sep. 25, 2001.

(51) Int. Cl.
*C12N 1/20* (2006.01)
*C12N 5/00* (2006.01)
*C12N 5/06* (2006.01)
*C12N 15/63* (2006.01)

(52) U.S. Cl. ............. 435/252.2; 435/325; 435/326; 435/455

(58) Field of Classification Search ............. 435/252.3, 435/455, 325, 326
See application file for complete search history.

(56) References Cited

FOREIGN PATENT DOCUMENTS

WO      WO 99/15199      *   4/1999

OTHER PUBLICATIONS

Bednarik et al., Proc. Natl. Acad. Sci. vol. 86, pp. 4958-4962, Jul. 1989.*

* cited by examiner

*Primary Examiner*—Robert B. Mondesi
*Assistant Examiner*—Khatol Shahnan-Shah
(74) *Attorney, Agent, or Firm*—Pantentique, PLLC

(57) ABSTRACT

This application provides a method to establish and construct cell lines expressing pathogens without destruction of the host cells. The invention allows for the formation of cell lines for the purpose of continuous expression, release, and harvesting of the pathogen and maintain the consistency of the final biological pro duct. Although the invention is intended for pathogen antigen expression, the invention allows for the production of any antigen by the described methods. The establishment of a chronically infected celline can be used for reagent, diagnostic, quantification, or vaccine purposes. We have used the procedure to select for a host cell line that naturally adapts to HIV-1 replication without affecting the host cell's ability to survive. This allowed for the establishment of a chronic HIV-1 expressing cell line that continuously expresses HIV-1 particles.

17 Claims, 1 Drawing Sheet

Established Chronic HIV-Expressing Cell Lines For Production of HIV Antigens and Nucleic Acids Lane 1: Standard protein molecular weight markers
Lane 2: Lysate of cell line without HIV
Lane 3: Concentrated culture supernatant from chronic cell line

CHRONIC PATHOGEN-EXPRESSING CELL LINES

RELATED APPLICATION

This application claims priority to U.S. Provisional Application No. 60/324,825 filed Sep. 25, 2001. The content of the application is herein incorporated by reference in their entirety.

PRIORITY DOCUMENTS

This application is a 371 application of PCT/US02/30197, filed Sep. 24, 2002, which claims priority to U.S. Provisional application 60/324,835, filed Sep. 25, 2001.

FIELD OF THE INVENTION

This invention relates to the field of reagents and diagnostics for the preparation of pathogen antigen, DNA, and RNA for pathogen detection and quantification by the formation and establishment of stable chronically expressing pathogen containing cell lines.

BACKGROUND OF THE INVENTION

Most, if not all pathogens, destroy their host cell during pathogen replication. Death of living cells can follow more than one possible scenario. It may result from an external injury, from cell killing during acute infection with cytopathic pathogens, or it may be the outcome of activating an internal pathway for cell suicide—programmed cell death. Programmed cell death or apoptosis is a controlled process by which unwanted cells are selectively eliminated. Apoptosis is a normal physiological process of eliminating unwanted cells from living organisms during embryonic and adult development, but can also be induced in cells following exposure to a pathogen.

The mechanism by which pathogens cause cell death—either direct killing or indirect—varies with the pathogen and the host cell in question. Controversy surrounds the cause of pathogen-induced cell death in even in the most extensively studied pathogens. For example, in human immunodeficiency virus type 1 (HIV-1)-initiated killing of CD4+ cells T cell death has been reported to be caused by syncytium formation-interaction of the envelope glycoprotein (gp120) with CD4 and subsequent fusion of the cells; influenced by type 1/type 2 cytokine modulation; mediated by specific cell death proteases (caspases) that function in the distal portions of the proteolytic cascades involved in apoptosis; membrane tumor necrosis factor induced cooperative signaling of tumor necrosis factor membrane receptors p55 and p75; Fas-induced apoptosis; and direct interaction of HIV gp120 envelop with the T cell CD4 molecule. Although agreement in the mechanism of cell death is disputed, it is clear that pathogen replication results in host cell destruction.

Pathogens replication can only occur inside host cells, commandeering the cell's machinery to reproduce. Infection typically begins when a pathogen encounters a cell with a specific cellular surface receptor molecule that matches the proteins found on the virus. The membranes of the virus and the cell will fuse, followed by release of viral nucleic acids, proteins and enzymes into the cell. Cell-to-cell spread of the pathogen also can occur through the fusion of an infected cell with an uninfected cell. The pathogen nucleic acid moves to the cell nucleus, where in most cases is spliced into the host DNA (for RNA-based pathogens, pathogen encoded reverse transcriptase converts RNA into DNA). Once incorporated into the cellular genome, RNA copies are made that are read by the host cell protein-making machinery. After the MRNA is processed in the cell nucleus, it is transported to the cytoplasm. The pathogen co-opts the cellular protein-making machinery to make long chains of viral proteins and enzymes, using the pathogen MRNA as a template. Newly made pathogen proteins, enzymes and nucleic acids gather inside the cell, while the pathogen envelope proteins aggregate within cellular membranes. An immature viral particle forms and pinches off from cellular membranes, acquiring an envelope. Depending on the pathogen, the mature virus particle is either released into the cytoplasm of the cell or released external to the cell.

In the case of HIV-1, the outer coat of the virus, known as the viral envelope, is composed of 72 copies (on average) of a complex HIV protein that protrudes from the envelope surface. This protein, known as Env, consists of a cap made of three or four molecules called glycoprotein (gp) 120, and a stem consisting of three or four gp41 molecules that anchor the structure in the viral envelope. Within the envelope of a mature HIV particle is a bullet-shaped core or capsid, made of 2,000 copies of another viral protein, p24. The capsid surrounds two single strands of HIV RNA, each of which has a copy of the virus genes—nine genes in total. Three of these, gag, pol and env, contain information needed to make structural proteins for new virus particles. The env gene, for example, codes for a protein called gp160 that is broken down by a viral enzyme to form gpl20 and gp41, the components of Env. Three regulatory genes, tat, rev and nef, and three auxiliary genes, vif, vpr and vpu, contain information necessary for the production of proteins that control the ability of HIV to infect a cell, produce new copies of virus, or cause disease. The core of HIV also includes a protein called p7, the HIV nucleocapsid protein; and three enzymes that carry out later steps in the virus life cycle: reverse transcriptase, integrase and protease. Another HIV protein called p17, or the HIV matrix protein, lies between the viral core and the viral envelope.

The ability to either molecularly clone and subsequently express a gene by recombinant technology, isolate whole pathogens, or purify specific pathogen gene(s), has led to the development of sensitive assay systems for detecting pathogens and for measuring immune responses to their infection. Because early pathogen infection often causes no symptoms, a doctor or other health care worker relies on testing a person's blood for the presence of antibodies (disease-fighting proteins) to the pathogen in question for diagnosis. By early testing, treatment at a time when the individuals' immune systems are most able to combat the pathogen and thus prevent the spread the virus to others could occur. Medical diagnose of pathogen's infection is normally performed by using two different types of antibody tests, ELISA and Western Blot. Diagnostic studies with a number of pathogens show that pathogen burden predicts disease progression. That is, people with high levels of pathogen in their bloodstream are more likely to develop pathogen-related symptoms or to die than individuals with lower levels of pathogen. Methods are available to detect specific antigens or nucleic acid sequences. These techniques can detect pathogen exposures that occur before antibody responses are established. Diagnostic detection for most pathogens exist in first-, second-, and third-line screening procedures and the use of Western Blot analysis is routinely established as a recognized confirmatory method.

SUMMARY OF THE INVENTION

This invention provides for the formation and establishment of stable chronically expressing pathogen cell lines for the preparation of pathogen antigens and nucleic acids. The established cell lines continually express the pathogen and contain the pathogens DNA stably integrated into the host cells DNA without detrimental effects on cellular viability. Once the line is established, reproducible preparations of pathogen antigens and nucleic acids can be prepared for reagent and diagnostic purposes. The invention is intended for in vitro use for the purpose of pathogen detection and quantification, although purification of native antigens and/or amplification of specific pathogen nucleic acid sequences, therapeutic vaccines, and monitoring or elucidating immune responses in vitro or in vivo can also be envisioned.

Establishing continually expressing pathogen antigen(s) cell lines has several advantages over procedures utilizing direct infection of host cell lines for obtaining enriched preparations of pathogen antigens and nucleic acids. Established lines allow reproducibility between preparations by controlling the rate, amount, and level of pathogen antigen transcription and translation. By fixing the number of pathogen genome integration sites in an established cell line (a process that is essentially uncontrollable when cells are directly infected) the level of antigen expression is controlled and synchronize. Synchrony can be achieved by enhancing expression coordinately by treatment with know inducers that up-regulate transcriptional and/or translational/post-translational events. However, even without induction, continuous expression and assemble of virus particles released from cells that cumulate in the culture media during expansion can significantly increase pathogen antigen yields. The chronic expressing pathogen containing cell lines can be established by standard infection procedures, transfection of pathogen containing nucleic acid sequences, transduction of pathogen containing nucleic acid sequences, or by genetically engineering the pathogen antigen of interest by recombinant techniques and assembling the pathogen antigen within a pathogen structures different from the natural native pathogen structure for that antigen of interest. Swapping of pathogen antigens or hybrid chimeric pathogen constructions could be extremely useful for preparations of pathogen antigens that are either not able to be grown, poorly expressed, or poorly released from cellular membranes in culture [such as, but not limited to hepatitis A, B, C, human herpesvirus (HHV)-6, -7, -8 viruses]. In addition, swapped or hybrid pathogen constructions could be a means to express pathogens whose structures are unstable during production and/or purification of the native pathogen that naturally express that antigen (such as, but not limited to Rubella). The present invention simplifies the process of pathogen antigen production over direct infection of host cells by decreasing: (i) labor, (ii) manipulation time, and (iii) expense associated with pathogen antigen production by establishing a process that is generic in design.

In one aspect, the invention provides a pathogen antigen preparation containing and expressing all possible antigens by either the introduction of the pathogen by direct infection with the pathogen itself, or transfection by chemical and/or mechanical means by the introduction of a molecular clone of the pathogen into a pre-screened cell line shown to be resistant to or capable of adapting to pathogen antigen expression that are normally detrimental to cell survival. In one embodiment of this aspect, the molecular clone or a nucleic acid preparation containing the pathogen genetic sequence is introduced into a cell line by transfection, which bypasses the cellular membrane to gain access to the cellular chromatin structure. Integration occurs and the cell adapts to the pathogen cytopathic deleterious effect on the cell by decreasing (down-regulating) or eliminating the pathogen cell surface membrane receptors. By this process or by other processes (presently identified or not) that similarly result in the ability of the pathogen-harboring-cell to survive and propagate in culture, a chronically expressing pathogen containing cell line is established (see EXAMPLE 1). In another embodiment, the established pathogen containing line is induced by chemical or mechanical means to enhance the production (on the DNA, RNA, protein, or release level) of pathogen output and hence, the ultimate yield of the pathogen antigens. Yield enhancement could occur by one or more inducers (chemical, mechanical or biological) added simultaneously or sequentially in order to obtain the desired results (see EXAMPLE 2).

In another aspect, the invention provides a method to virally transduce [including but not limited to murine leukemia virus (MuLV), adenovirus, adeno-associated virus (AAV), lentivirus, and canarypox vectors] specific pathogen antigen(s) into a cell line for the purpose of over-expressing one or more of the pathogen antigens. In one embodiment of this aspect, the transduced specific pathogen antigen is membrane-bound in the transduced cell in such a fashion that the pathogen antigen will be specifically incorporated or acquired (by either a passive or active process). In this embodiment, the transduced over-expressed pathogen antigen(s) associate with expressed competent intact virus or virus-like particle (VLP) core structures. Association of the specific pathogen antigen(s) with the released competent intact virus—replication competent, or not—or VLP could be enhanced by the inclusion of known sequences in a hybrid recombinant construction with the pathogen antigen, but these hybrid constructions are not necessarily required. These specific sequences could be intracellular/transmembrane sequences or sequences identified to enhance the association of the pathogen antigen to the competent intact virus or VLP. In addition, the competent intact virus or VLP that provides the "carrier function" for the pathogen antigen need not be related to the pathogen antigen in question, but could be a heterologous competent intact virus and/or VLP. However, it could be the pathogen and/or VLP itself and in that case (where the "carry function" is being performed by a VLP of the pathogen), the hybrid recombinant construction with the pathogen antigen could be required for VLP release from the cell. Preferably, the transduced cell line is an established cell line expressing either competent intact viruses or VLP, although it could be a cell line where establishment of the chronic competent intact virus or VLP is introduced after pathogen antigen transduction (see EXAMPLE 3). The invention allows for the "swapping" of antigens with similar functions between pathogen and hybrid constructions, where fusion molecules are created for the purpose of expressing specific pathogen antigens within the backbone structure of another pathogen. The second pathogen provides only a carrier function and is there solely for the expression of the specific pathogen antigen of interest. The swapping or inclusion of antigens could be variant-forms of the same pathogen antigen (see EXAMPLE 4). This concept allows pathogen antigen cassettes to be created for specific antigens of interest into a particular carrier platform (see EXAMPLE 5).

In another aspect the invention provides a reproducible source of pathogen specific nucleic acid preparations of DNA and RNA for detection and quantification purposes. This nucleic acid material could be used in nucleic acid based detection and/or quantification test systems as a positive control reagent, but need not be limited to this role. The number of copies of pathogen-specific sequences could be quantified by comparing signal intensities (ELISA-based probe-dependent readings) with cloned fragments after oligonucleotide-dependent polymerase chain reactions (PCR) assays. For RNA, a reverse transcriptase step would be performed prior to PCR analysis. In another embodiment of this aspect, instead of using the purified nucleic acids with known copy number, intact virus particles obtained from harvested supernatants of chronic pathogen containing cell lines could be quantified for pathogen nucleic acid copy number and used in known amounts "spiked" into duplicate samples to determine percent recovery of pathogen specific material from human specimens and/or tissues. In this way the present invention can serve as reagent material for both antigen-based and nucleic acid-based detection kits for the research and diagnostic industry.

In another aspect the invention relates to any antigen that could be expressed on, in, or within a virus or virus-like-particle. In one embodiment of this aspect, the antigen is a tumor antigen for a particular form of cancer and used as a diagnostic indicator for progression of the disease. In another embodiment of this aspect, the tumor antigen is a therapeutic product and used to alert the immune system to mount a response against the tumor (see EXAMPLE 6). The invention allows the expression of any protein used for reagent, diagnostic, research, or therapeutic purposes assembled into a virus or virus-like-particle that is released from an established chronically expressing cell line for the purpose of harvesting the antigen by collecting and/or concentrating the virus or virus-like-particle released into the culture supernatant. The major advantage of associating the antigen with a virus or virus-like-particle is the ease of recovering said antigen at a lower cost using generic technology to harvest the antigen when associate with a particle released from an established expressing cell line rather than the antigen released in a soluble-form. Once harvested from the culture supernatant, the antigen-associated particle could be used directly, the particle could be disrupted to form a lysate, or the antigen could be partially and/or fully purified from particle associated material by standard methods used in the art of protein purification. Harvesting could be by ultracentrifugation or by low-speed centrifugation either by differential sedimentation or in combination with techniques to remove or precipitate particulate material from culture fluids. The invention improves current methods of antigen production by providing a method that increase yield, stability, and concentrates antigens of interest. Once concentrated, downstream processing and/or purification of the antigen(s) are simplified. This aspect expands the concept of antigen production from pathogen antigens to the production of any antigen/protein of choice.

In summary, the formation and establishment of stable chronically expressing pathogen containing cell lines has a wide range of applications, including but not limited to, in vitro preparation of pathogen antigens, DNA, and RNA for pathogen detection and quantification for use as reagents in diagnostic test for research and industry. The present invention provides a method to form pathogen expressing cell lines. These lines are formed by either direct infection by standard methods or by bypassing cell surface receptors to introduce the pathogen nucleic acid material into a cell of choice. The cell of choice could be prescreen to tolerate the continuous expression and assemble of pathogen particles that are released from the cell, or can be introduced into a cell that does not naturally express the receptor needed for entry, or can be genetically modified to harbor and expression the host pathogen by specific addition or deletion of signals that maintains cellular viability. Specific pathogen antigens can be expressed: (i) as the entire pathogen integrated into the cellular chromatin structure; (ii) as a specific pathogen antigen whose expression is required for the assemble of the pathogen particle; or (iii) as a specific pathogen antigen that associates with another pathogen strain (related or distal to the pathogen of interest) that provides a carrier function to said pathogen antigen. In the latter two cases, the pathogen antigen can be unmodified containing its innate sequence or could be genetically modified by standard procedures to enhance its incorporation into either homologous or heterologous pathogen particles. Thus, disclosed are methods for the formation and establishment of chronic expressing pathogen containing cell lines.

The present invention particularly concerns:

A method for establishing a cell line that expresses a pathogen to levels 10-to 1,000-fold greater than that attained by standard procedures of direct infection and expansion. This level of pathogen production is attained by establishing conditions to generate multiple integration of the pathogen genome into the host cell line, maintaining the cell line through the critical period of adaptation to tolerate this level of pathogen production, elucidating through experimentation the sequence and timed additions of reagents to the culture to further increase pathogen production, and elucidating a method for efficient intact pathogen isolation.

BRIEF DESCRIPTION OF THE DRAWINGS

The invention is further described by the accompanying drawings and the description thereof herein, although neither is a limitation of the scope of the invention.

DETAILED DESCRIPTION OF THE PREFERRED EMBODIMENTS

Figure 1:
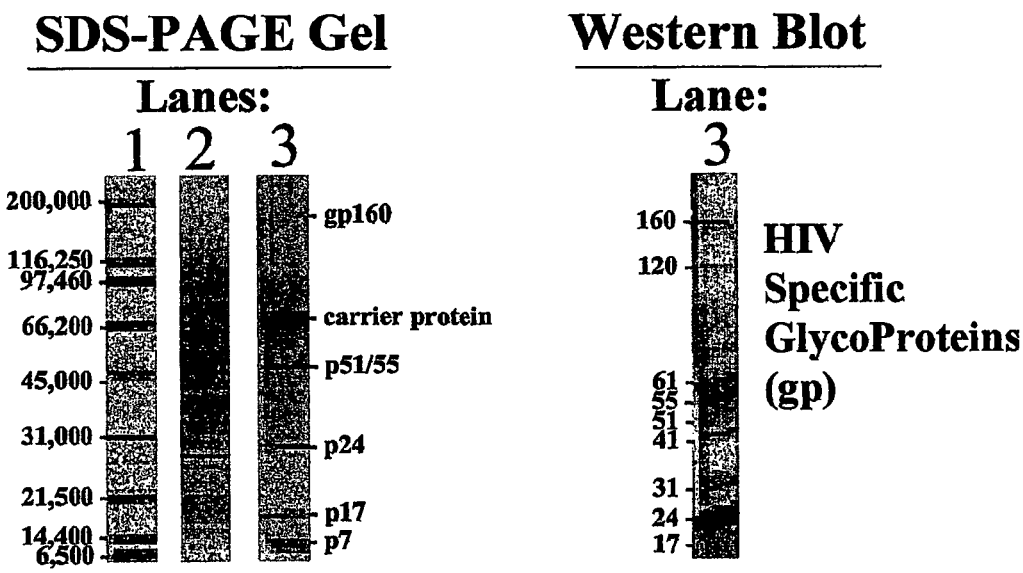
FIG. 1 shows analysis by SDS-PAGE gel electrophoresis (Lane 2) of protein bands associated with proteins endogenous to an uninfected CD4 positive T-lymphocyte cell line (A3.01), and (Lane 3) the absence of cellular proteins in lysates (detergent disrupted preparation) made from particles released into the culture fluid of the same CD4 positive cell line that chronically expresses human immunodeficiency virus type-1 (HIV-1$_{HXB2}$) particles. Further analysis of the HIV-1 containing lysate by Western Blot illustrates the detection and the presence of all HIV-1 processed and unprocessed proteins. The env gene codes for a protein called gp160 that is broken down by a viral enzyme to form gp120 and gp41, the components of Env. The gag gene codes a precursor p61/55/51 that is then cleaved to p24 and p17—the HIV matrix protein; the pol gene codes for the p31 protein.

The present invention relates to the establishment of cell lines containing and expressing pathogens that have been constructed in such a way as to not kill the host cell. The cell lines maintain continuous pathogen expression without cellular destruction, because the cells are modified or adapted in such a way that pathogens that are normally detrimental to the cell are no longer detrimental to the cell due to said changes in cellular physiology. The pathogen could be the entire pathogen genome integrated in the host cell line, or be composed of sequences expressing a pathogen antigen(s) of interest that is dependent on packaging and exportation from a given cell by a virus dependent carrier process. In the case of the entire pathogen genome, expression of the pathogen is dependent on the intrinsic ability of the pathogen to assemble pathogen particles that are released from the cell without cellular destruction. Pathogen expression without cell death allows for continuous pathogen expression and accumulation of the pathogen particles in the culture supernatant. The pathogen particles can be collected by procedures of ultracentrifugation or preferably by selective dehydration and precipitation (use of polyethylene glycol or similar agents), affinity and/or size dependent chromatography: (i) to increase yield; (ii) to prevent shearing of external pathogen antigens from the pathogen surface during pathogen harvest and concentration; (iii) to decrease costs associated with labor, equipment, and machinery; (iv) to decrease the volume of culture supernatant required to obtain the same quantities of pathogen needed by more conventional methods. By harvesting the said pathogens by these non-conventional methods the final product is improved, allowing better performance, over a shorter period of time, and at lower production costs. Conventional method of large-scale pathogen formation where the pathogen is infected into a host cell line with the addition of uninfected cells to support pathogen propagation, monitoring the infection to insure viral spread, maintenance and release of the pathogen, and continuous flow ultracentrifugation are all eliminated. The conventional process is replaced with a process generic in design—cellular expansion of an established pathogen containing cell line, followed by low-speed centrifugation harvest.

The present invention relates to, but is not limited to, reagents and diagnostics. The enriched pathogen preparation can be inactivated by standard procedures (that include, but not limited to UV-AMT, gamma-irradiation, zinc-finger inhibitors) that maintain pathogen particle integrity for use in vaccine preparations in vivo, therapeutic immune enhancement in vivo or in vitro, a reagent to monitor therapeutic or immune responses in vivo or in vitro, and for quantification and/or detection purposes. For similar therapeutic, diagnostic, and/or reagent use, the enriched pathogen preparation can be detergent disrupted and use as a lysate containing pathogen antigens, DNA, and RNA for protein and nucleic acid purification, or as a partial fractionated or unfractionated pathogen containing preparation. The present invention provides for use of intact or disrupted pathogens as an immunoprophylactic, immunotherapeutic, or vaccine candidate to treat, for example, infectious diseases, cancer, neurological disorders, exposure to toxins, and as an alternative to conventional drug and/or antibiotic therapies on which host resistance has developed. In pursuant of the present invention, HIV-1 was chosen as an example of a pathogen in which a permanent cell line continuously expressing HIV-1 was established. However, permanent cell line expressing any pathogen can be established. Although the introduction of the entire pathogen genome may generally be desired, in some cases, whether it is due to the cells selected or to the pathogen being expressed, nuances related to the pathogen life cycle or expressed genes, the invention can also relate to virus-like-particles (VLPs). Noninfectious viral particles can also be engineered to contain structural core proteins that assemble or acquire specific pathogen antigen(s) either homologous or heterologous to the viral structural core proteins. These synthetic particles do not replicate, but rather produce pseudovirions that carry a particle pathogen antigen(s) that are released from the cell and allow harvesting of the pathogen from the culture supernatant in a non-infectious form. The invention is envisioned as a general way of constructing and expressing pathogen antigens. Virus and/or virus-like-particles are easier to produce and purified than recombinant pathogen antigens and as such the present invention has advantages over recombinant procedures to produce pathogen antigens. Production of these antigens in mammalian cells further insures appropriate post-modification (that include, but not limited to glycosylation, polyADP-ribosylation, myristylation) of the pathogen antigen—modifications that enhance antibody-antigen reactivity/avidity and induction of immune responses.

The chronic expressing pathogen containing cell lines described herein establish an ideal system for obtaining enriched preparations of pathogen antigen, DNA, and RNA that could be used in assessing the presence of a pathogen in human tissues and/or bodily fluids. Those infected with a pathogen usually respond to the pathogen by stimulating the production of antibodies against proteins coded by the pathogen. Diagnose of pathogen infection can be determined by antibody testing. Large numbers of samples are screened by enzyme-linked immunosorbent assay (ELISA) analysis to evaluate the presence of antibodies in the general population of samples being tested. Further testing of positive samples are required and recommended by testing positive samples with assays demonstrating increased sensitivity and specificity; Western Blot analysis often function as such a confirmatory test. These diagnostic tests, whether for clinical or research purposes, require pathogen material in the form of a lysate to detect the specific pathogen infection. Since it may take antibodies against a pathogen as long as six months to be produced, diagnostic assays based on the presence of pathogen antigen and/or nucleic acids are also being developed, in addition to antibody-based testing. These assays detect the pathogen itself, instead of the immune response against the pathogen. Further tests being developed are measuring the ability of the patients' immune system to respond to a pathogen. These responses can form the bases of vaccine and/or therapeutic intervention strategies to test the ability of an intervention or preventative experimental procedures to demonstrate efficacy in an individual before initiating the study—a putative entrance criteria. The present invention is intended as a consistent supply of pathogen-derived material for the above purposes.

Pathogens against which the present invention may be applicable in the formation of chronic pathogen antigen(s) expressing cell lines include, but are limited to bacteria, parasites, protozoa, fungi, prion, and viruses. Viruses are infectious agents (pathogens) including hepatitis B, hepatitis C, herpes simplex virus, varicella zoster, Epstein-Barr virus, cytomegalovirus, human herpesvirus-6, -7, -8, HIV-1, HIV-2, HTLV-1, HTLV-2, Rubella, Rubeola, Influenza, Rotavirus, West Nile, Dengue and other emerging flaviviruses. Prions are the transmissible pathogenic agents responsible for diseases such as scrapie, bovine spongiform encephalopathy, and associated human diseases. Fungi, protozoa and parasites include Toxoplasma, trypanosomes, babesia, rickettsia, malaria, and enteric pathogens. Bacteria include species of *Chlamydia, Helicobacter, Neisseria, Mycobacteria,* (especially *M. tuberculosi*). The scientific literature identifies 1,415 species of infectious organism known to be pathogenic to humans, including 217 viruses and prions, 538 bacteria and rickettsia, 307 fungi, 66 protozoa and 287 helminthes. Out of these, 868 (61%) are zoonotic, that is, they can be transmitted between humans and animals, and 175 pathogenic species are associated with diseases considered to be "emerging". Over 100 viruses have been associated with acute central nervous system infections, causing among other diseases encephalitis and meningitis; Nipah virus in Malaysia and neurovirulent enterovirus (70 strains) that cause severe neurological disease; vector borne disease agents include Japanese encephalitis, Barmah Forest, Ross River, and Chikungunya viruses; hendra virus, formerly called equine morbillivirus a rabies-related virus, Australian bat lyssavirus, and a virus associated with porcine stillbirths and malformations, Menangle virus. Most emerging viruses are zoonotic and because of the large number of present and emerging pathogens that infect human are zoonotic, veterinary viral-delivered vaccinology strategies are also encompassed within the scope of the invention.

Antigens against which the present invention may be applicable in the formation of chronic antigen(s) expressing cells lines include polypeptides encoded by the pathogen listed above. The multitudes of antigens encoded by these agents that may be expressed include, but are not limited to external surface proteins and structure proteins including enzymes, transcription factors, and other cell regulatory molecules. For example, antigens encoded by any genes of the HIV-1 genome including gag, pol vif vpr, vpu, tat, rev, env, and nef may be all present as either intact antigens or immune dominate peptides. Another example is the pathogenic prion protein (PrPSc) template and endogenous cellular prion protein (PrPC). In addition, tumor antigens are included in the scope of this invention. Two types of antigens have been identified on tumor cells: Tumor-specific transplantation antigens (TS-TAs) that are unique to cancer cells, and tumor-associated transplantation antigens (TATAs) that are found on both cancer and normal cells. Thus, tumor antigens consist of TSTAs, TATAs, and oncogene proteins. Tumor-specific antigens have been identified on tumors induced by chemical and physical carcinogens and some virally induced tumors. The antigen(s) can be present within the chronic expressing pathogen containing cell line as part of an infectious process, naturally native to the cell, transduced or transfected by biological (viral vectors), chemical (liposomes), or mechanical (electroporation) methods. The pathogen antigen could be expressed and assembled into the pathogen itself, or associated with a different pathogen particle.

The following examples further illustrate experiments using established chronic pathogen containing cell lines that have demonstrated reduction to practice and utility of selected preferred embodiments of the present invention, although they are in no way a limitation of the teachings or disclosure of the present invention as set forth herein.

EXAMPLE 1

Electroporation of a Molecular Clone of HIV-1$_{HXB2}$ into a Cell Line Screened to Support HIV-1 Expression while Maintaining Host Cell Survival and Propagation Establishment of a cell line that continuously produces and expresses infectious HIV-1 demonstrates the principle of this invention.

A series of transformed CD4 positive T-lymphocyte cell lines were tested by infection of the cells with infectious HIV-1 and determining the ability of the cells to continue to grow in culture. All lines infected with HIV-1 expressed virus as monitored by p24 antigen capture assay analyses and after 2 to 4 weeks stopped growing, appearing to die. Cultures were keep in a 37° C. incubator for an extended period of time and one cell line after 3 months started to grow as first detected by a change in the color of the media (from deep red to yellow) due to the oxidation of phenol-red present in the media. This line was further propagated by the addition of fresh media and assayed for HIV-1 coded p24 released into the supernatants of the culture. The assay showed the presence of HIV-1, suggesting that the recovered cells were propagating in the presence of the continuous expression of HIV-1.

To increase the number of copies (and presumably virual expression) of HIV-1 integrated into the cellular genome, a molecular clone of HIV-1—HXB2, was electroporated into the uninfected parental cell line. The parental line was the CD4 positive T-lymphocyte cell line, A3.01, that propagated in the presence of continuous HIV-1 expression. The procedure introduces the viral genome into the host cell for integration into the host cell chromatin structure; bypassing the usual CD4 receptor mediated entry of this pathogen into cells. After months of incubation at 37° C., a cell line immersed that propagated HIV-1 continuously without cell death. The cell population was cloned in 96-well microtiter plates by limited-dilution and the cell line established. A Western Blot of a lysate of particles released from this cell line exposed to a HIV-1 positive plasma sample is shown in FIG. 1.

This line is unlike any HIV-containing cell line previously made (which include, for example ACH-2 and U1) in that expression of infectious virus does not require induction. This cell line constitutively express >4×10$^6$ picograms of p24 antigen per milliliter within the first 16 hours (>0.4 ug/rl/hr) when cultured in fresh media.

EXAMPLE 2

Established Chronic HIV-Expressing Cell Lines can be further Induced to Increase Pathogen Expression The principle of this invention is further demonstrated by the ability to enhance HIV-1 pathogen expression by physical, chemical and/or biological methods.

Conditions were established to transiently further increase HIV-1 production from the established continually HIV-1 expressing cell line. Different inducers in combination and at different times of addition were tested to determine the maximal expression of HIV-1 possible from the established continual HIV-1 expressing cell line. The result of an experiment is shown in the accompanying table.

TABLE 1

| Treatment | HIV-1 p24 Antigen Expression (per ml per 2days) |
|---|---|
| without | 20 ug |
| with 1,000 × conc. | 290 ug 12 mg |

The ability to grow, induce, and concentrate an enriched preparation of the HIV-1 pathogen to over 10 mg per liter of supernatant allows gram quantities of this pathogen from 100 liters of culture.

EXAMPLE 3

Transduction of Cells with Specific Pathogen Antigen(s) and Incorporation of the Antigen(s) into a Virus or a Virus-Like-Particle The principle of this invention could be further demonstrated by experiments using established pathogen expressing cell lines transduced with a heterologous pathogen antigen or antigens that are incorporated or acquired by a virus particle during virus assembly and is therefore released from the cell and can be recovered in the supernatant. The assembled virion could be an infectious pathogen or a non-infectious virus-like-particle. Furthermore, the heterologous pathogen antigen or antigens could contain sequences that would allow specific incorporation into the assembling virion as a prerequisite for virion release or to insure association with the released virion. The heterologous pathogen antigen or antigens could be expressed as a membrane bound molecule on the transduced established pathogen expressing cell lines where it would be displayed on the released virion surface or could be non-membrane bound and associate with the released virion core structure.

EXAMPLE 4

Transduction of a Pathogen Antigenic Region from Different Strains or Isolates to Broad or Direct Immune Responses The principle of this invention could be further demonstrated by experiments where modified antigenic sequences are transduced into pathogen established cell line in order to broad or enhance the immune response. This approach could be most useful with pathogens that are continually changing to evade immune responses or to pathogens strains or isolated found prevalent to a particle geographical area. An example is HIV/AIDS disease and Influenza/Flu disease (but not limited to these pathogens), where viral coat protein evades host immune responses by sequence variations. In this case, different envelope sequences could be expressed and displayed on the same virus particle.

EXAMPLE 5

Construction of Hybrid Envelope Cassette Structures that Assembled into a Virus Particle within a Viral Packaging Cell Line The principle of this invention could be further demonstrated by experiments using hybrid envelope cassette cloning vectors where an established packaging cell line is constructed. The cloning vector would allow an in-phase translational reading of the pathogen antigen fused to an intracellular-transmembrane sequence that is incorporated into the virus by the components supplied by the established packaging cell line. This would be most useful for those pathogens that are either hard to grow, not fully characterized, or difficult to purify. Examples of such pathogen include, but not limited to rubella and hepatitis, where the surface antigens of these pathogens could be cloned and expressed on a virus assembled in a retrovirus, herpesvirus, or other vector within an established packaging cell line.

EXAMPLE 6

Transduction of Tumor Antigens and Inclusion into Cellular Releases Particles

The principle of this invention could be further demonstrated by experiments using established cell lines expressing virus or virus-like-particle incorporating a tumor antigen called Globo H. This antigen is found on the surface of many cancers, including prostrate and breast cancer. Chronic cell lines expressing Globo H could be constructed and the particles released from the cell and harvested from the culture supernatant could be used as reagents for diagnostic purposes or therapeutically for the induction of immune responses.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as maybe applied to the essential features herein before set forth.

What is claimed is:

1. A biologically constructed cell line modified to chronically produce budding particles, said cell line comprising
components for production of said budding particles, said components comprising an integrated exogenous gene which expresses an antigen of an infectious pathogen;
wherein said cell line chronically produces non-infectious budding particles comprising said antigen.

2. The biologically constructed cell line of claim 1 wherein said cell line tolerates the continuous expression and assembly of intact budding particles.

3. The biologically constructed cell line of claim 2 wherein said intact budding particles are released into the cell line culture supernatant.

4. The cell line of claim 1 wherein said exogenous gene expresses a protein, a polypeptide, an antibody, a glycolipid, a lipid, a pathogen, a tumor, or an infectious agent.

5. The cell line of claim 1 wherein said components are introduced by infection into said cell line.

6. The cell line of claim 3 wherein said components are recombinantly introduced by an expression vector into the host cell line.

7. The cell line of claim 1 wherein said components are recombinantly introduced by an expression vector into the host cell line.

8. The cell line of claim 4, wherein said pathogen is the entire pathogen.

9. The cell line of claim 4, wherein said infectious agent is the entire agent.

10. A method for establishing a cell line according to claim 1, said method comprising integrating an exogenous gene which expresses an antigen of a pathogen and
recombinantly introducing components into said cell line to produce non-infectious budding particles that comprise said antigen.

11. The cell line of claim 1 wherein said particles are human immunodeficiency virus type 1 particles.

12. The cell line of claim 1 wherein said budding particles further comprise at least one antigen fragment associated with a primary surface molecule and at least one co-stimulatory molecule.

13. The cell line of claim 12 modified to express a molecule (s) that can inhibit a human pathogen.

14. The cell line of claim 13 wherein said pathogen is biological.

15. The cell line of claim 1 wherein said antigen is an HIV-1 antigen.

16. The cell line of claim 1 wherein said antigen is presented on said particles and capable of initiating an immune response.

17. The cell line of claim 1 wherein said exogenous gene expresses a hybrid chimera of antigens from more than one infectious pathogen.

* * * * *

UNITED STATES PATENT AND TRADEMARK OFFICE
CERTIFICATE OF CORRECTION

PATENT NO.        : 7,662,608 B2                               Page 1 of 1
APPLICATION NO. : 10/486415
DATED             : February 16, 2010
INVENTOR(S)       : Joseph D. Mosca It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 676 days.

Signed and Sealed this

Twenty-eighth Day of December, 2010

David J. Kappos
*Director of the United States Patent and Trademark Office*